US011339402B2

(12) United States Patent
Fang et al.

(10) Patent No.: US 11,339,402 B2
(45) Date of Patent: May 24, 2022

(54) RICE ENVIRONMENTAL CONDITIONAL-LETHAL MUTANT GENE OSES11, ENCODING PROTEIN AND USE THEREOF

(71) Applicant: Northeast Institute of Geography and Agroecology, Chinese Academy of Science, Heilongjiang (CN)

(72) Inventors: Jun Fang, Heilongjiang (CN); Jing Wang, Heilongjiang (CN); Yang Yu, Heilongjiang (CN); Qingyun Bu, Heilongjiang (CN)

(73) Assignee: Northeast Institute of Geography and Agroecology, Chinese Academy of Science

( * ) Notice: Subject to any disclaimer, the term of this patent is extended or adjusted under 35 U.S.C. 154(b) by 0 days.

(21) Appl. No.: 16/962,192

(22) PCT Filed: Nov. 11, 2019

(86) PCT No.: PCT/CN2019/117126
§ 371 (c)(1),
(2) Date: Jul. 14, 2020

(87) PCT Pub. No.: WO2020/119359
PCT Pub. Date: Jun. 18, 2020

(65) Prior Publication Data
US 2021/0062211 A1     Mar. 4, 2021

(30) Foreign Application Priority Data
Dec. 10, 2018    (CN) .......................... 201811503381.X

(51) Int. Cl.
*C12N 15/82*     (2006.01)
*C07K 14/415*    (2006.01)

(52) U.S. Cl.
CPC ........ *C12N 15/8267* (2013.01); *C07K 14/415* (2013.01)

(58) Field of Classification Search
None
See application file for complete search history.

(56) References Cited

FOREIGN PATENT DOCUMENTS

| CN | 102121017 A | 7/2011 |
|----|-------------|--------|
| CN | 105821074 A | 8/2016 |

(Continued)

OTHER PUBLICATIONS

Genbank Accession No. AK106196.1. *Oryza sativa* Japonica Group cDNA clone:001-208-E11, full insert sequence. (Year: 2008).*
Chen R. et al., "Rice UDP-Glucose Pyrophosphorylase1 is Essential for Pollen Callose Deposition and Its Cosuppression Results in a New Type of Thermosensitive Genic Male Sterility", The Plant Cell, vol. 19:847-861, 2007.

(Continued)

*Primary Examiner* — Matthew R Keogh
*Assistant Examiner* — David R Byrnes
(74) *Attorney, Agent, or Firm* — Brian M. Kaufman; Robert D. Atkins; Atkins and Associates, P.C.

(57) ABSTRACT

Disclosed are rice environmental conditional-lethal mutant gene osesl1, an encoding protein and use thereof The gene osesl1 has a nucleotide sequence shown as SEQ ID NO: 1 in the Sequence Listing. The encoding protein thereof has an amino acid sequence shown as SEQ ID NO: 2. After heading of osesl1 mutant rice, seed embryo lethal phenotype appears at 12 days after pollination, exhibiting darkening at the junction between embryo and endosperm. When an average temperature is below 22° C., a seed embryo is normal; when the average temperature is above 28° C., the seed embryo is lethal; when the temperature is between 22° C. and 28° C., the seed embryo is lethal under long daylight conditions (>13 h) and normal under short daylight conditions (<13 h). Use of the gene osesl1 in controlling seed embryo development of rice is further provided.

7 Claims, 5 Drawing Sheets
Specification includes a Sequence Listing.

(56) References Cited

FOREIGN PATENT DOCUMENTS

| CN | 107418956 A | 12/2017 |
|---|---|---|
| WO | 2006021558 A2 | 3/2006 |
| WO | 2012004795 A1 | 1/2012 |
| WO | 2013023623 A1 | 2/2013 |

OTHER PUBLICATIONS

Ding J. et al., "A long noncoding RNA ergulates photoperiod-sensitive male sterility, an essential component of hybrid rice", PNAS, vol. 109, No. 107, pp. 2654-2659, 2012.

Jian S. et al., "*Oryza sativa* Myosin XI B controlls pollen development by photoperiod-sensitive protein localizations", Developmental Biology, 304:579-592, 2007.

NCBI Predicted: *Oryza sativa* Japonica Group phospho-2-dehydro-3-deoxyheptonate aldolase 1, chloraplastic-like (LOC4345872, mRNA, NCBI Reference Sequence: XM_015794667.1, pp. 1-3, Aug. 7, 2018.

Zhang, H. et al., "Mutation in CSA creates a new photoperiod-sensitive genic male sterile line applicable for hybrid rice seed production", PNAS, vol. 110, No. 1, pp. 76-81, 2013.

Zhang, Z. et al., "Genetic Analysis on the Sterility in Indica PGMRs HN5s", Acta Agranomica SINICA, vol. 28, No. 1, pp. 131-135, 2002.

Zhou, H., et al., "Photoperiod- and thermo-sensitive genic male sterility in rice are caused by a point mutation in a novel noncoding RNA that produces a small RNA", Cell Research, 22:649-660, 2012.

Zhou, H., et al, "RNase Zs1 processes UbL40 mRNAs and controls thermosensitive genic male sterility in rice", Nature Communications, 5:4884, pp. 1-9, 2014.

\* cited by examiner

SEQUENCE LISTING

<160> NUMBER OF SEQ ID NOS: 7

<210> SEQ ID NO 1
<211> LENGTH: 1518
<212> TYPE: DNA
<213> ORGANISM: artificial sequence
<220> FEATURE:
<223> OTHER INFORMATION: Rice environmental conditional-lethal mutant gene osesl1

<400> SEQUENCE: 1

```
atgcccctcg cgccatgccc ctcgccgccc ctccctcct ccccgtggcc ggcgcgcgcc      60
ccgcgccggg gcggcctcct ccgcgcccgc gcggtgcggg cggcgccccg gccgccgagc     120
aagtggtcgc tgggtagctg gcgcagcctg acggcgctgc agcagccgga gtaccccgac     180
aaggcggagc tggatgaggt gctccggacg gtggaggcgt tcccgccgat tgtcttcgcc     240
ggcgaggcgc gcaagctgga ggagcggctc gcggaggccg ccgtcgggcg cgcgttcctc     300
ctccagggcg gcgactgcgc cgagagcttc aaggagttta acgcgaacaa catccgggac     360
accttccgtg tgctcctcca gatgtccgtg ttgctcatgt ttggaggcca gatgcctatc     420
atcaaggtag aagaatggc aggtcagttt gcaaagccaa ggtcagatgg ctttgaggag     480
agggatggag tgaagttgcc aagctacaga ggggataaca ttaatgggga ttcattcgat     540
gagaaatcaa gattgccaga tccacaccgc atgatcaggg catactcaca gtctgcagca     600
acactgaatt tgctgcgggc ttttgctact ggaggttatg ctgccatgca gagggtaaca     660
caatggaacc ttgacttcac agagcatagt gaacagggtg acaggtacat ggagctggct     720
caccgagttg atgaggcttt ggggttcatg gcagctgctg gtctcactat ggaccatcct     780
attatgacaa caacagaatt ctggacatca catgagtgcc ttcttcttcc ctatgagcaa     840
gcacttactc gcgaggattc cacatctggc ctctattacg actgttctgc tcacttcctt     900
tgggttggag agcgtacacg tcagcttgat tgtgcccatg tggagtttct ccgaggaatt     960
gcgaaccctc tgggtatcaa ggtcagtgac aagatggacc caaaagaact tgtgaagttg    1020
attgatatct tgaatcccca gaacaaacca gggagaatta ctatcattac aagaatggga    1080
cctgaaaaca tgagagtgaa actccctcac ctaatacgtg ctgtccgtgg tgctggccag    1140
atagtaacat gggttactga tccgatgcat ggtaacacaa tgaaggctcc ttgtggcctc    1200
aagactcgct cctttgatag aatcttggct gaggtgcgcg cattctttga tgtgcacgaa    1260
caagaaggca gccacccagg aggggtgcat ctggagatga ctggacaaaa tgtgacagaa    1320
tgcatcggcg ggtcacgcac ggtgacattc gacgatctgg gctcacgata ccacacacac    1380
tgcgacccga ggctcaacgc atcgcagtct ctggagttgg cgttcatcat cgccgagcgg    1440
```

```
ctcagaaaga ggaggatcgc ctcatggcag ttgaacaaga acagtcatct gggcaacatc    1500
ccatctttgg ggctctga                                                  1518
```

<210> SEQ ID NO 2
<211> LENGTH: 505
<212> TYPE: PRT
<213> ORGANISM: artificial sequence
<220> FEATURE:
<223> OTHER INFORMATION: Rice environmental conditional-lethal mutant
      gene osesl1-encooding protein

<400> SEQUENCE: 2

```
Met Pro Leu Ala Pro Cys Pro Ser Pro Leu Pro Ser Ser Pro Trp
1               5                   10                  15

Pro Ala Arg Ala Pro Arg Arg Gly Gly Leu Leu Arg Ala Arg Ala Val
            20                  25                  30

Arg Ala Ala Pro Arg Pro Pro Ser Lys Trp Ser Leu Gly Ser Trp Arg
        35                  40                  45

Ser Leu Thr Ala Leu Gln Gln Pro Glu Tyr Pro Asp Lys Ala Glu Leu
    50                  55                  60

Asp Glu Val Leu Arg Thr Val Glu Ala Phe Pro Pro Ile Val Phe Ala
65                  70                  75                  80

Gly Glu Ala Arg Lys Leu Glu Glu Arg Leu Ala Glu Ala Ala Val Gly
                85                  90                  95

Arg Ala Phe Leu Leu Gln Gly Gly Asp Cys Ala Glu Ser Phe Lys Glu
            100                 105                 110

Phe Asn Ala Asn Asn Ile Arg Asp Thr Phe Arg Val Leu Leu Gln Met
        115                 120                 125

Ser Val Leu Leu Met Phe Gly Gly Gln Met Pro Ile Ile Lys Val Gly
    130                 135                 140

Arg Met Ala Gly Gln Phe Ala Lys Pro Arg Ser Asp Gly Phe Glu Glu
145                 150                 155                 160

Arg Asp Gly Val Lys Leu Pro Ser Tyr Arg Gly Asp Asn Ile Asn Gly
                165                 170                 175

Asp Ser Phe Asp Glu Lys Ser Arg Leu Pro Asp Pro His Arg Met Ile
            180                 185                 190

Arg Ala Tyr Ser Gln Ser Ala Ala Thr Leu Asn Leu Leu Arg Ala Phe
        195                 200                 205

Ala Thr Gly Gly Tyr Ala Ala Met Gln Arg Val Thr Gln Trp Asn Leu
    210                 215                 220

Asp Phe Thr Glu His Ser Glu Gln Gly Asp Arg Tyr Met Glu Leu Ala
225                 230                 235                 240

His Arg Val Asp Glu Ala Leu Gly Phe Met Ala Ala Ala Gly Leu Thr
                245                 250                 255

Met Asp His Pro Ile Met Thr Thr Thr Glu Phe Trp Thr Ser His Glu
            260                 265                 270

Cys Leu Leu Leu Pro Tyr Glu Gln Ala Leu Thr Arg Glu Asp Ser Thr
        275                 280                 285

Ser Gly Leu Tyr Tyr Asp Cys Ser Ala His Phe Leu Trp Val Gly Glu
    290                 295                 300

Arg Thr Arg Gln Leu Asp Cys Ala His Val Glu Phe Leu Arg Gly Ile
305                 310                 315                 320

Ala Asn Pro Leu Gly Ile Lys Val Ser Asp Lys Met Asp Pro Lys Glu
                325                 330                 335

Leu Val Lys Leu Ile Asp Ile Leu Asn Pro Gln Asn Lys Pro Gly Arg
```

```
              340             345             350
Ile Thr Ile Ile Thr Arg Met Gly Pro Glu Asn Met Arg Val Lys Leu
            355                 360                 365

Pro His Leu Ile Arg Ala Val Arg Gly Ala Gly Gln Ile Val Thr Trp
        370                 375                 380

Val Thr Asp Pro Met His Gly Asn Thr Met Lys Ala Pro Cys Gly Leu
385                 390                 395                 400

Lys Thr Arg Ser Phe Asp Arg Ile Leu Ala Glu Val Arg Ala Phe Phe
                405                 410                 415

Asp Val His Glu Gln Glu Gly Ser His Pro Gly Gly Val His Leu Glu
            420                 425                 430

Met Thr Gly Gln Asn Val Thr Glu Cys Ile Gly Gly Ser Arg Thr Val
        435                 440                 445

Thr Phe Asp Asp Leu Gly Ser Arg Tyr His Thr His Cys Asp Pro Arg
    450                 455                 460

Leu Asn Ala Ser Gln Ser Leu Glu Leu Ala Phe Ile Ile Ala Glu Arg
465                 470                 475                 480

Leu Arg Lys Arg Arg Ile Ala Ser Trp Gln Leu Asn Lys Asn Ser His
                485                 490                 495

Leu Gly Asn Ile Pro Ser Leu Gly Leu
            500                 505

<210> SEQ ID NO 3
<211> LENGTH: 3751
<212> TYPE: DNA
<213> ORGANISM: artificial sequence
<220> FEATURE:
<223> OTHER INFORMATION: Genome of rice environmental conditional-lethal
      mutant gene osesl1

<400> SEQUENCE: 3
atgcccctcg cgccatgccc ctcgccgccc ctcccctcct cccgtggcc  ggcgcgcgcc      60 ccgcgccggg gcggcctcct ccgcgcccgc gcggtgcggg cggcgccccg gccgccgagc     120
aagtggtcgc tgggtagctg gcgcagcctg acggcgctgc agcagccgga gtaccccgac     180
aaggcggagc tggatgaggt gctccggacg gtggaggcgt tcccgccgat tgtcttcgcc     240
ggcgaggcgc gcaagctgga ggagcggctc gcggaggccg ccgtcgggcg cgcgttcctc     300
ctccagggcg gcgactgcgc cgagagcttc aaggagttta cgcgaacaa  catccgggac     360 accttccgtg tgctcctcca gatgtccgtg ttgctcatgt ttggaggcca gatgcctatc     420
atcaaggtat aaaattaccc ccgaatatct tatttattcc ccttttta at catatcttac     480 tataaagtta tccccacaaa ctccttaagc ttatcatgca agatgccac  atcatcgtcc     540 actaacaaga tgccacatca tcatccacta attaacaaga tgccacatta tcatccacta     600
acaatcatca catttaaaca tcatgcaata tagtttttat aatttaagag cttttcaaat     660
acaaacatgt taaattatca tccaaaataa ttcacaaaat gttttaatat atatcttta t    720 tatgttttat gatatcctat atatttatat agttcatcct cacttagtta gtgcttaaat     780
gattaatcta tggtccaaat tatctttctc attttttcct ctaattaagt catatcacat     840
caattgtttt tagcctttag atgattaatc tatggtccaa actatctccc tacttttctt     900
cttccataaa gtcataccac cttacttttt acgtttgaat caccattcta catactattt     960
aaatttaaat tatcataaac cacattaatt tacttaatct tatgttatct agctatctta    1020
catgttattt tttttactgt tatcatacta aattcccaca gcaatgcgcg gggtttcacc    1080
```

```
tagtaataat aataattatg tctcgctaca aaaactgtag attttttgtat tcagcatcac  1140
aatgtaatag gaagaattgc agtctaattt actgcacctc gaattatttg acaagtactt  1200
ataattttta tgcatttgtg aaagaactta cttgttcaat cacaaatgtt tacattgttg  1260
ttctcttgtt ttgttgtacc aagaactgaa agccaaatca attttgtttt tctgatcagt  1320
ttgcactaca cagttcacac aaaggattta tcggtttgtg tacacgatta gatgagtata  1380
tttagtgcat gttcttaatt aggttggcac aataaatctt tcacaagcgt cctttacttg  1440
atgttaaata ctgtaataga agaacccttg tcctggtcga tattctgtat tgtcattcaa  1500
cttctgcaat cttcttttgc ttgattctct ttttacaatg caaattaact gtataagtgt  1560
atactctaat catgatatat gtttcaactt tcaactgtat gtaccaaaat ttccattgct  1620
aggtatttcc tgcaaatgga acaaatctgt agctgtatca tggattgaat tttcttttct  1680
cctgttacca tgttgttttt gcgttccttt aatgcatttc tagtggacat cgcacagaat  1740
tgtatcactt actgtctcac atggaatatg taggtaggaa gaatggcagg tcagtttgca  1800
aagccaaggt cagatggctt tgaggagagg gatggagtga agttgccaag ctacagaggg  1860
gataacatta tgggggattc attcgatgag aaatcaagat tgccagatcc acaccgcatg  1920
atcagggcat actcacagtc tgcagcaaca ctgaatttgc tgcgggcttt tgctactgga  1980
ggttatgctg ccatgcagag ggtaacacaa tggaaccttg acttcacaga gcatagtgaa  2040
cagggtgaca ggtggttacc tttatcttaa actgtcccaa ttcttcattg attgcttctc  2100
agatgaattg attcatgtaa ttcatttaag ccacagccat atgctcacca ctgcaattct  2160
tgtacaatgt tgaacaggta catggagctg gctcaccgag ttgatgaggc tttgggggttc  2220
atggcagctg ctggtctcac tatggaccat cctattatga caacaacaga attctggaca  2280
tcacatgagt gccttcttct tccctatgag caagcactta ctcgcgagga ttccacatct  2340
ggcctctatt acgactgttc tgctcacttc cttttgggttg gagagcgtac acgtcagctt  2400
gattgtgccc atgtggagtt tctccgagga attgcgaacc ctctgggtat caaggtaaat  2460
aggaatattc ctacacttgt caagacagat aaatagataa tgtataccaa gttcaaactt  2520
catttgaaag tgcaggtaat tcacactttg tcctaaagga attcacccta aactcatcaa  2580
actaaatgca ggtcagtgac aagatggacc caaaagaact tgtgaagttg attgatatct  2640
tgaatcccca gaacaaacca gggagaatta ctatcattac aagaatggga cctgaaaaca  2700
tgagagtgaa actccctcac ctaatacgtg ctgtccgtgg tgctggccag atagtaacat  2760
gggttactga tccgatgcat ggtaacacaa tgaaggctcc ttgtggcctc aagactcgct  2820
cctttgatag aatcttggta attccttgca tggcctacag cctacttttc agtatttgct  2880
tgttcctatt acttctcagt ggtctgtaac tgagcaatag tcttatattt gctggacagc  2940
ctaattgcat atgcactatg ctgctatgca gtgagaagct gtttataggg tgtttcatga  3000
tggaactaaa cattataata tatctgaaac aacatagctt tgtcaaaatg atggttctcg  3060
tttatgcaga atgtggtagg acactagtgg ctagagtttg ccaattgcca ttcatatatg  3120
aataactatc aacacttgaa acaaaatgcg tgtaaaagtg catgacaaag agcaatcgtc  3180
tatagctctg tcatggtttc atggaccgtg aatctagttc attttcacta tgactggtat  3240
tacttcgttg tagtagtttg gttgttctct tgctattcaa cagttcctat catctaccag  3300
ccgtagttta ggataaaaatc tgagactttt cactgctatg gttcagtcct tgggagaagt  3360
atcgtacacg tttaaacttc tactatacta ttcatttgac attaacatga ccggcgactt  3420
aaatcaacta agatgactta tgttgccttc ttgaaaccag gctgaggtgc gcgcattctt  3480
```

```
tgatgtgcac gaacaagaag gcagccaccc aggaggggtg catctggaga tgactggaca    3540
aaatgtgaca gaatgcatcg gcgggtcacg cacggtgaca ttcgacgatc tgggctcacg    3600
ataccacaca cactgcgacc cgaggctcaa cgcatcgcag tctctggagt tggcgttcat    3660
catcgccgag cggctcagaa agaggaggat cgcctcatgg cagttgaaca agaacagtca    3720
tctgggcaac atcccatctt tggggctctg a                                   3751

<210> SEQ ID NO 4
<211> LENGTH: 20
<212> TYPE: DNA
<213> ORGANISM: artificial sequence
<220> FEATURE:
<223> OTHER INFORMATION: Primer OsESL1 F

<400> SEQUENCE: 4
atgcccctcg cgccatgccc                                                  20

<210> SEQ ID NO 5
<211> LENGTH: 20
<212> TYPE: DNA
<213> ORGANISM: artificial sequence
<220> FEATURE:
<223> OTHER INFORMATION: Primer OsESL1 R

<400> SEQUENCE: 5
gagccccaaa gatgggatgt                                                  20

<210> SEQ ID NO 6
<211> LENGTH: 29
<212> TYPE: DNA
<213> ORGANISM: artificial sequence
<220> FEATURE:
<223> OTHER INFORMATION: Primer Os08g0484500 F

<400> SEQUENCE: 6
ttacccggga tgcccctcgc gccatgccc                                        29

<210> SEQ ID NO 7
<211> LENGTH: 29
<212> TYPE: DNA
<213> ORGANISM: artificial sequence
<220> FEATURE:
<223> OTHER INFORMATION: Primer Os08g0484500 R

<400> SEQUENCE: 7
ccgtctagag agccccaaag atgggatgt                                        29
```

RICE ENVIRONMENTAL CONDITIONAL-LETHAL MUTANT GENE OSES11, ENCODING PROTEIN AND USE THEREOF

FIELD OF THE INVENTION

The present application relates to a rice mutant gene osesl1, an encoding protein and use thereof.

BACKGROUND OF THE INVENTION

Rice (*Oryza sativa* L.) is an important grain crop upon which human depend, and more than half of the world population live on rice. Rice is grown in more than 120 countries worldwide; particularly, Asia has 90% of the planting areas and rice yield. China is a world's big rice producer and has a long history of rice culture, and is one of the largest rice production bases; the total rice yield ranks first in the world. In recent years, many problems arise, such as increase of the world population, intensification of old aging, acceleration of urbanization construction, and environmental deterioration caused by vegetation destruction in some areas. Therefore, how to raise the rice yield and quality and guarantee food security under limited human and environmental resource conditions is a major issue concerning the national economy and people's livelihood.

Raising the rice yield and quality through heterosis is one of the main achievements in modern agriculture, and three- and two-line hybrid ricecultivars are put forward based on male sterility. In three-line method, a male sterile line exhibits stable sterility and is not affected by illumination and temperature; however, a maintainer line is needed to multiply seeds, leading to a complex production process; moreover, a restorer line is limited by cytoplasmic biological inheritance, restricting the development of the three-line method. The core of the two-line method is a photo-thermo-sensitive male sterile line, and fertility alteration thereof is closely related to sunshine duration and temperature: the fertility alteration of a thermo-sensitive male sterile line is mainly dependent upon temperature control, i.e., high temperature induces sterility, and low temperature induces fertility; the fertility alteration of a photoperiod sensitive male sterile line is principally controlled by photoperiod, i.e., long photoperiod induces sterility, and short photoperiod induces fertility. The two-line hybrid rice does not need breeding of the male sterile line by means of the maintainer line, featuring simple seed production and low costs; however, with the increase of reproductive generations and the rising of threshold temperature, the male sterile line loses thermo-sensitivity and is susceptible to unsettled weather, so that fertility fluctuation leads to a decrease in seed purity. Thus, seed production and multiplication are risky.

So far, a plurality of thermosensitive or photoperiod-sensitive genes cloned from male sterile lines, including: thermo-sensitive male sterile gene tms5, where a protein thereof encodes a short RNaseZ homologous protein RNaseZ$^{S1}$ (Zhou H, Zhou M, Yang Y, et al. 2014. RNase ZS1 processes UbL40 mRNAs and controls thermosensitive genic male sterility in rice. Nature Communications, 5: 4884.); photoperiod-sensitive male sterile gene pms3, which is an RNA (LDMAR) (Ding J, Lu Q, Ouyang Y, et al. 2012. A long noncoding RNA regulates photoperiod-sensitive male sterility, an essential component of hybrid rice. Proceedings of the National Academy of Sciences of the USA, 109(7): 2654-2659); photo-thermo-sensitive genic male sterile gene Ugp1 (UDP-glucose pyrophosphorylase 1) (Chen R, Zhao X, Shao Z, et al. 2007. Rice UDP-glucose pyrophosphorylase1 is essential for pollen callose deposition and its co-suppression results in a new type of thermo-sensitive genic male sterility. The Plant Cell, 19(3): 847-861.); *Oryza sativa* myosin XIB (osmyo XIB) (Jiang S Y, Cai M, Ramachandran S. 2007. *ORYZA SATIVA* MYOSIN XI B controls pollen development by photoperiod-sensitive protein localizations. Developmental Biology, 304(2): 579-592.); and carbon starved anther (CSA) (Zhang H, Xu C, He Y, et al. 2013. Mutation in CSA creates a new photoperiod-sensitive genic male sterile line applicable for hybrid rice seed production. Proceedings of the National Academy of Sciences of the USA, 110(1): 76-81.). All of the above genes relate to pollen fertility related genes. Presumptively, an environment-sensitive zygotic lethal gene or an embryonic lethal gene is introduced into a male sterile line, and environmental conditions can be used to kill self-pollinated seeds produced by the male sterile line during seed production. Even if unsettled weather leads to fertility alteration and thus fruiting, conditional lethal zygotes or embryos will cause the self-pollinated seeds to fail to survive, guaranteeing the hybrid purity. However, during the seed multiplication of the male sterile line, pollen fertility conditions further meet survival conditions of zygotes or embryos, guaranteeing the fruiting and availability of self-pollinated seeds. However, scientific researchers have not found appropriate and available genes yet.

In the process of seed production of three- or two-line hybrid rice, both male sterile and restorer lines should be seeded separately; moreover, when harvesting hybrids, restorer lines should even be harvested separately. Either condition has such problems as tedious operation, high cost, and high labor intensity. Therefore, the three- or two-line hybrid rice is merely suitable to be popularized in labor-intensive countries and regions, but is slowly popularized in economically developed and highly mechanized countries, substantially restricting the development of hybrid rice. Under limited human and environmental resource conditions, realizing entire mechanization of hybrid rice seed production is a must to guarantee an increase in hybrid rice yield and cost reduction. Therefore, special materials with fertilization and fruiting barriers or inbred but ablastemic materials are put forward to screen as male parents, where both types of materials can provide pollen normally. Selecting such materials as restorer lines (male parents) saves individual treatment of restorer lines during hybrid rice seed production, but breeding of male parents per se remains to be studied, which therefore have not been used in production yet. Hence, how to prevent the effect of abnormal climate on fertility of photo-thermo-sensitive male sterile line effectively and minimize costs of hybrid rice seed production is an important task that has to be solved in hybrid rice production in China.

SUMMARY OF THE INVENTION

To resolve the problem that the existing methods fail to effectively prevent the influence of abnormal climate on fertility of photo-thermo-sensitive male sterile line, the present application provides a rice environmental conditional-lethal mutant gene osesl1, an encoding protein and use thereof.

In one aspect, the present application provides a rice environmental conditional-lethal mutant gene osesl1, having a nucleotide sequence shown as SEQ ID NO: 1 in the Sequencing List. The gene has five exons and four introns.

In another aspect, the present application provides a protein encoded by the rice environmental conditional-lethal mutant gene osesl1 according to claim 1, having an amino acid sequence shown as SEQ ID NO: 2.

In another aspect, the present application provides use of the rice environmental conditional-lethal mutant gene osesl1 in controlling seed embryo development of rice.

Further, a seed embryo is normal when rice growth is controlled at an environmental temperature below 22° C., and lethal when rice growth is controlled at an environmental temperature above 28° C.

Further, when rice growth is controlled at an environmental temperature between 22° C. and 28° C., the seed embryo is lethal if sunshine duration is >13 h, and normal if the sunshine duration is <13 h.

The present application extracts DNA from a genome of osesl1 mutant; using dCAP2 as a marker, an osesl1 osesl1 genotype homozygote is obtained by PCR amplification and recognition by restriction endonuclease NcoI. An upstream primer labeled with the dCAP2 has a sequence shown as SEQ ID NO: 4, and a downstream primer has a sequence shown as SEQ ID NO: 5.

After observation and investigation of the osesl1 mutant in the present application, it is found that after heading of rice, seed embryo lethal phenotype appears at 12 days after pollination, exhibiting darkening at the junction between embryo and endosperm. When an average temperature is below 22° C., a seed embryo is normal; when the average temperature is above 28° C., the seed embryo is lethal; when the temperature is between 22° C. and 28° C., the seed embryo is lethal under long daylight conditions (>13 h) and normal under short daylight conditions (<13 h).

The present invention obtains a EMS-mutagenized environmental conditional-lethal mutant osesl1 (photo/thermoperiod sensitive lethal 1) in japonica rice *Oryza sativa* "Nipponbare". In view of the mutant, seed embryos darken after fruiting, preharvest sprouting in hot and humid weather at the harvest. However, the seed embryo is normal when rice grows in short daylight and cold temperature condition, and there is no effect on vegetative and reproductive growth of rescued plants. This mutant phenotype is regulated by a recessive genic gene. By constructing a hybrid population, a gene regulating this trait is obtained by map-based cloning. Sequence comparison indicates that the gene encodes an entrance enzyme of shikimate pathway—3-deoxy-D-arabino-heptulosonate 7-phosphate synthase (DAHPS). So far, no one has reported that such gene mutation influences seed embryo darkening and environmental conditional death, suggesting that this is a new function that the gene regulates the seed embryo development under the influence of the environment. Obtaining the mutant is of important application value in understanding the mechanism of rice embryo development. Clone mutant gene can be explored to use to breed hybrid rice male sterile lines and restorer lines and protecting local varieties. The rice environmental conditional-lethal mutant gene in the present invention: changes environmental conditions to kill seed embryos, guaranteeing the seed purity of male sterile lines in two-line method; is used in two- and three-line restorer lines under the same conditions to improve the mechanization degree of hybrid rice; and further introduces the mutant gene into local varieties in regions with lethal conditions to protect the local varieties according to regional photoperiod and temperature characteristics.

DETAILED DESCRIPTION OF THE DRAWINGS

Figure 1:
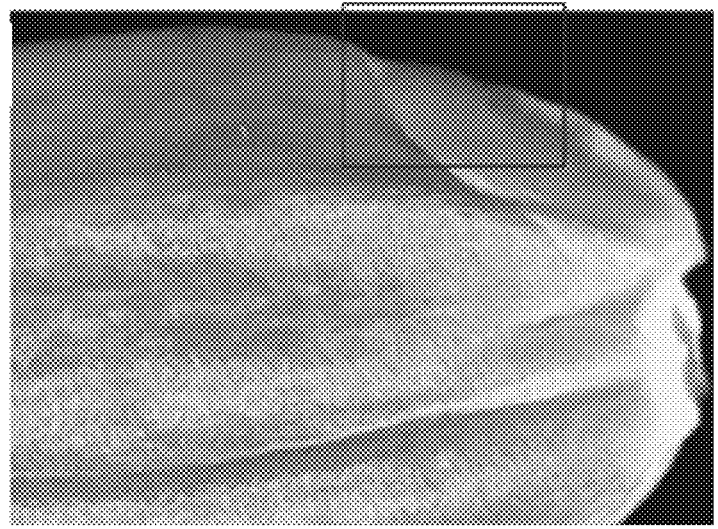
FIG. 1 illustrates a seed embryo of wild-type *Oryza sativa* "Nipponbare" at 12 days after pollination.

The technical solution of the present invention is not limited to the specific implementations listed below, and includes any combination between the specific implementations.

Specification implementation 1: A rice environmental conditional-lethal mutant gene osesl1 in the example has a nucleotide sequence shown as SEQ ID NO: 1 in the Sequencing List. The gene has five exons and four introns.

Specification implementation 2: A protein encoded by the rice environmental conditional-lethal mutant gene osesl1 in the example has an amino acid sequence shown as SEQ ID NO: 2.

Specification implementation 3: The example describes use of the rice environmental conditional-lethal mutant gene osesl1 in controlling seed embryo development of rice.

Specification implementation 4: A difference between this implementation and specific implementation 3 is that: seed embryos are normal when rice growth is controlled at an environmental temperature below 22° C., and the seed embryos are lethal when rice growth is controlled at an environmental temperature above 28° C. Others are consistent with those in specific implementation 3.

Specification implementation 5: A difference between this implementation and specific implementation 3 is that: when rice growth is controlled at an environmental temperature between 22° C. and 28° C., seed embryos are lethal if sunshine duration is >13 h, and normal if the sunshine duration is <13 h. Others are consistent with those in specific implementation 3.

In the following, examples of the present invention will be described in detail. The examples are implemented on the premise of the technical solution of the present invention, and the detailed examples and specific operation processes are given, but the protection scope of the present invention is not limited to the following examples.

EXAMPLE 1

Obtaining and Phenotype Analysis of Rice Environmental Conditional-Lethal Mutant osesl1

Figure 2:
FIG. 2 illustrates a section of the seed embryo of wild-type *O. sativa* "Nipponbare" at 12 days after pollination.
Figure 3:
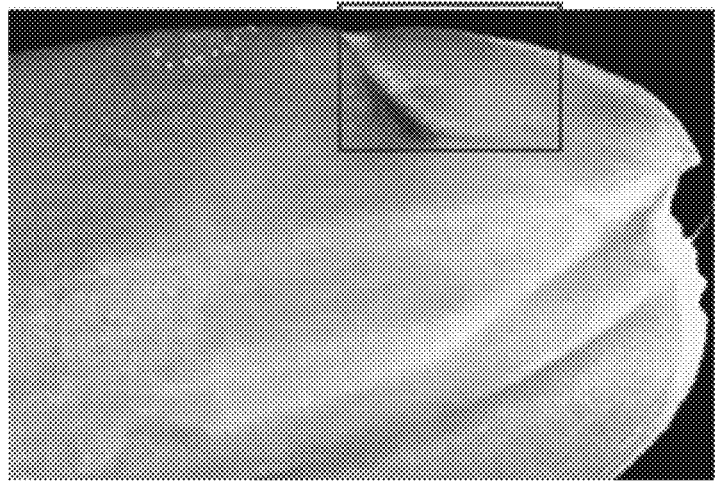
FIG. 3 illustrates an osesl1 mutant seed embryo at 12 days after pollination.
Figure 4:
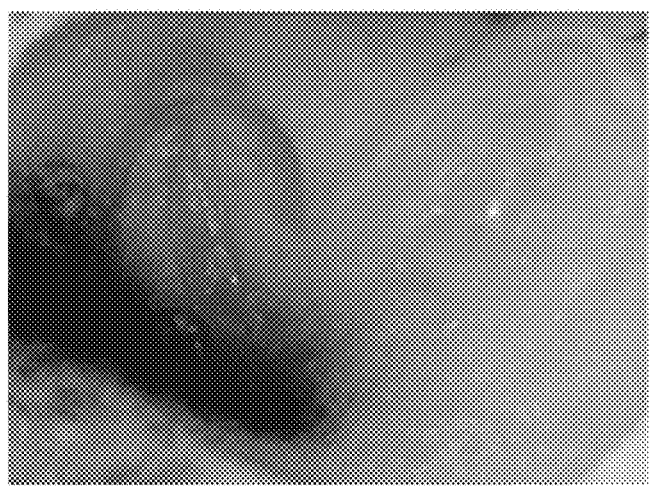
FIG. 4 illustrates a section of the seed embryo of the osesl1 mutant at 12 days after pollination.

Rice environmental conditional-lethal mutant osesl1 was obtained from seeds of EMS-mutagenized japonica rice Oryza sativa "Nipponbare". Treatment included the following steps: soaking seeds in ultrapure water for 24 h at room temperature until imbibition; subsequently, soaking seeds in 1.5% EMS (v/v) for 18 h; washing seeds with 75 ml of ultrapure water thrice, each for 5 min, followed by 75 ml of ultrapure water thrice, each for 20 min. Seeds were rinsed with tap water for 2 h before sowing. For detailed treatment method, refer to the following reference (Till B J, Cooper J, Tai T H, et al. Discovery of chemically induced mutations in rice by TILLING. BMC Plant Biology, 2007, 7(1):19). The mutagenized seeds were sowed in the field and M1-generation seeds were harvested; M1 generations inbred to obtain M2 generations, which were planted in Hainan (low temperature and short day) in winter and in Heilongjiang (high temperature and long day) in summer, respectively, so as to select mutants with normal breeding under short-day and low-temperature conditions and lethal seed embryos under long-day and high-temperature conditions therefrom. A mutant, osesl1, was selected. There was no significant difference in vegetative and reproductive growth between the mutant and Oryza sativa "Nipponbare" (control); at 12 days after flowering and pollination under long-day and high-temperature conditions, programmed cell death occurred at a junction between seed embryo and endosperm, resulting in darkening of the whole seed embryo, as shown in FIGS. 1 to 4. FIG. 1 illustrates a seed embryo of wild-type O. sativa "Nipponbare" at 12 days after pollination; FIG. 2 illustrates a section of the seed embryo of wild-type O. sativa "Nipponbare" at 12 days after pollination; FIG. 3 illustrates an osesl1 mutant seed embryo at 12 days after pollination; FIG. 4 illustrates a section of the seed embryo of the osesl1 mutant at 12 days after pollination. The mutant seeds with darkened seed embryos were not dormancy-broken, but were viable at 0 day after harvest, with a germination rate of 44.67%; at 60 days after harvest (DAH60), the germination rate decreased to 12.18%, and at 90 days (DAH90), the germination rate was 0, suggesting that all seeds were almost dead. In case of breaking dormancy at 45° C. for seven days, all seed embryos would die as well. Detailed statistical results are listed in Table 1.

TABLE 1

Statistical results of the germination rate of seed embryos.

| Germination | DAH0 | DAH 60 | DAH90 | DAH7 for 45° C. |
|---|---|---|---|---|
| Wild-type | 99.3% + 0.01% | 99.99% + 0.01% | 99.33% + 0.01% | 100.00% + 0.00% |
| osesl1 | 44.67% + 0.09% | 12.18% + 0.10% | 0.00% + 0.00% | 0.00% + 0.00% |

Using a backcross method, an osesl1 site was introduced into conventional japonica rice and indica rice cultivars, such as O. sativa "Minghui 63" (MH63 $^{osesl1}$), O. sativa "Chenghui 448" (CH448 $^{osesl1}$), O. sativa "7001S" (7001S $^{osesl1}$), etc. The osesl1 site had no effect on rice yield, suggesting that the osesl1 site could be used in different background. The osesl1 site was introduced into O. sativa "Kongyu 131" (KY131, a local japonica rice cultivar in Northeast China) to obtain KY131$^{osesl1}$ by backcrossing; the KY131$^{osesl1}$ was planted in long-day and high-temperature regions; vegetative and reproductive growth thereof were observed, and it was not significantly different from that of wild-type. Yield-related traits of KY131$^{osesl1}$, i.e., 1,000-grain weight and seed setting rate, were analyzed statistically and they were found that: differences in 1,000-grain weight and seed setting rate were not significantly different between KY131$^{osesl1}$ and wild-type KY131, there was an increase in number of seeds per plant, and lethality rate reached 93.3% (Table 2). By means of these characteristics, osesl1 genotype can be introduced into O. sativa "Kongyu 131" (KY131$^{osesl1}$, a patented rice cultivar in North China), and seeds thereof can be multiplied in Southern China by means of the lethal characteristic of embryo, providing variety protection for rice production in Northern China.

TABLE 2

Analysis of yield-related traits of KY131$^{osesl1}$ and KY131

| Cultivar | Number of seeds per plant | 1,000-Grain weight (g) | Seed setting rate (%) | Lethality (%) |
|---|---|---|---|---|
| KY131$^{osesl1}$ | 455.6 ± 119.6 | 20.3 ± 1.35 | 93.2% ± 1.30% | 93.3% ± 1.30% |
| KY131 | 374.4 ± 92.56 | 21.9 ± 1.21 | 93.8% ± 1.70% | 0.00% ± 0.00% |

EXAMPLE 2

Genetic Analysis and Map-Based Cloning of Rice Environmental Conditional-Lethal Mutant osesl1

(1) Genetic Analysis

Osesl1 mutant was hybridized with Oryza sativa "Minghui 63" (MH63) to obtain F1 seeds; 278 F2 population were obtained after F1 selfing, and phenotypes of F2 populations were investigated to calculate a segregation ratio, where the ratio of wild-type to mutant type was 216:62, and chi-square test satisfied a 3:1 segregation ratio; F2 populations backcrossed by osesl1 mutant and wild-type O. sativa "Nipponbare" were further investigated, and the result was also consistent with the 3:1 segregation ratio, suggesting that the phenotype of the mutant was regulated by a single recessive gene.

(2) Gene Mapping a) Initial mapping is conducted with an SSR molecular marker. First, rice SSR primers were synthesized according to the SSR sequence information published on RiceData; next, DNAs were extracted from parents and F2 generations (osesl1×MH63) using the CTAB method; finally, PCR amplification and polyacrylamide gel electrophoresis (PAGE) were conducted. With parents osesl1 and MH63 as controls, molecular markers analysis shows differences in F2 populations.

The CTAB method was used. Brief steps were as follows: placing approximately 0.1 g of leaves in a 2 ml EP tube, precooling in liquid nitrogen with steel balls, grounding under vibration, mixing well with 700 μl of DNA extract preheated at 65° C. carefully, incubating in a water bath at 65° C. for 40 min, mixing with isometric chloroform vigorously, and centrifuging (at 12,000 rpm) for 10 min; precipitating supernatant with isometric isopropanol for 30 min, centrifuging (at 12,000 rpm) for 10 min; washing precipitates with 70% absolute alcohol, centrifuging (at 12,000 rpm) for 5 min, discarding supernatant, and drying invertedly in the air; dissolving the precipitates with 50 μl of water; storing in a refrigerator at −20° C.

The total volume of a PCR system was 10 μl: rice genomic DNA template 1 μl (approximately 200 ng); 2× Master Mix 5 μl; 10 μM primers, each for 0.5 μl; diluting to 10 μl with ddH$_2$O. The reaction program was as follows: 35 cycles of denaturation at 94° C. for 5 min, 94° C. for 30 s, 58° C. for 30 s, and 72° C. for 20 s; and extension at 72° C. for 10 min.

Figure 5:
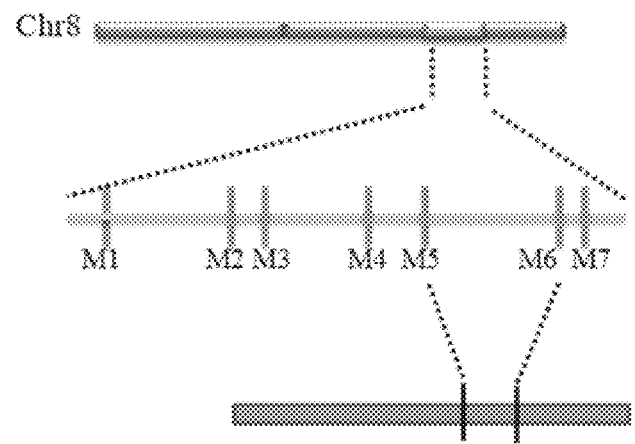
FIG. 5 illustrates initial mapping of the OsESL1 mutant gene.
Figure 6:
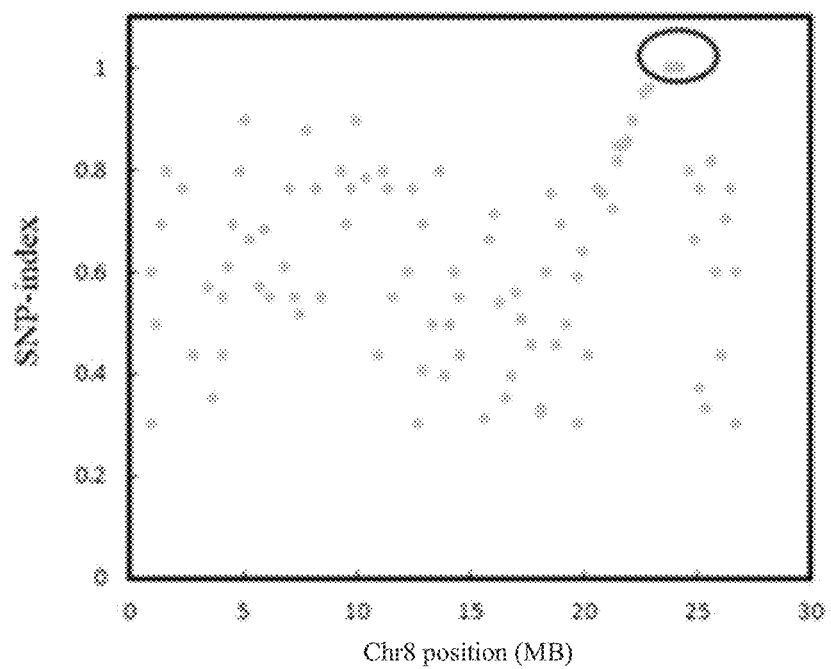
FIG. 6 illustrates fine mapping of the OsESL1 mutant gene.

Analysis result found that a mutant gene of the osesl1 mutant was initially mapped between markers M5 and M6 in linkage group 8 (FIG. 5).

b) Fine mapping was conducted by resequencing. F2 (osesl1×Nipponbare) populations were investigated and classified according to the presence of mutant phenotype; representative wild-type and mutant-type F2 individuals were screened to establish a wild-type pool and a mutant pool, respectively; DNAs were extracted by the CTAB method, respectively; a DNA pool was established for resequencing, thereby enabling fine mapping of mutant genes (FIG. 6); the DNA had been registered in The Rice Annotation Project (RAP) (accession number: Os08g0484500).

Flanking primers of the gene were designed according to the fine mapping result, followed by PCR amplification and sequencing. The total volume of a PCR system was 50 rice genomic DNA template 1 μl (approximately 200 ng); 2× PCR buffer for KOD Fx 25 μl; 2 mM dNTP 10 μl; KOD Fx (1U/μl) 1 μl; 10 μM primers, each for 1.5 μl; diluting to 50 μl with ddH$_2$O.

```
Primer OsESL1 F:
                                  (SEQ ID NO. 4)
5'-ATGCCCCTCGCGCCATGCCC-3'

Primer OsESL1 R:
                                  (SEQ ID NO. 5)
5'-GAGCCCCAAAGATGGGATGT-3'
```

The reaction program was as follows: 30 cycles of denaturation at 98° C. for 10 s, 60° C. for 90 s, and 68° C. for 2 min; and extension at 78° C. for 10 min. PCR products were recovered and analyzed by Sanger sequencing.

It was found that Os08g0484500 gene was an enzyme gene of shikimate pathway, i.e., OsDAHPS, where exon 1 has an SNP locus, which was a substitute for G-T, resulting in a missense mutation in Val(gtg)-leu(ttg). Therefore, the gene was named OsESL1. A mutant gene of the OsESL1, CDS (Coding Sequence), had a sequence shown as SEQ ID NO: 1; an encoding protein had a sequence shown as SEQ ID NO: 2; a genome had a sequence shown as SEQ ID NO: 3.

Example 3: Functional Marker Analysis

Figure 7:
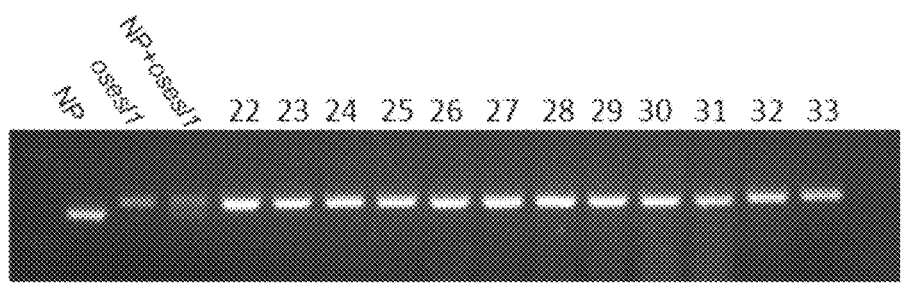
FIG. 7 illustrates dCAP2-labeled detection of wild-type, osesl1 mutant, and T2 transgenic individuals.

According to SNP loci of the sequencing result, dCAPS markers were designed by dCAPS Finder 2.0; genotypes of F2 (osesl1×Nipponbare) populations were screened and recognized by the dCAP2 markers.

dCAP2 primer had an upstream primer sequence shown as SEQ ID NO: 4 and a downstream primer sequence shown as SEQ ID NO: 5, with a genome DNA as template. The total volume of a PCR system was 10 μl: rice genomic DNA template 1 μl (approximately 200 ng); 2× Master Mix 5 μl; 10 μM dCAP2 primers, each for 0.5 μl; diluting to 10 μl with ddH$_2$O. The reaction program was as follows: 35 cycles of denaturation at 94° C. for 5 min, 94° C. for 30 s, 58° C. for 30 s, and 72° C. for 20 s; and extension at 72° C. for 10 min. Enzyme digestion was conducted with NcoI overnight at 37° C. Digested products were detected on 4% agarose. The wild type was restricted as 102 bp, while mutant types could not be restricted as 127 bp (FIG. 7). The method can be further useful in detecting osesl1 genotype introduced materials.

Detection results of F2 generations found a wild type/heterozygous type/mutant type separation ratio was 1:2:1, consistent with the Mendelian genetic law, suggesting that the SNP was tightly linked to the mutant phenotype of F2 generation, and that the mutant phenotype was determined by the mutation site.

EXAMPLE 4

Complementation Test for Phenotype of Rice Environmental Conditional-Lethal Mutant osesl1

(1) Construction and Genetic Transformation of Complementary Vector

To confirm whether the mutant phenotype was caused by the missense mutation in the base, genomic DNAs of "Nipponbare" and osesl1 mutant were used as templates, respectively, and Os08g0484500F and Os08g0484500R as primers,

```
Primer-Os08g0484500 F:
                                  (SEQ ID NO. 6)
5'-TTACCCGGGATGCCCCTCGCGCCATGCCC-3';

Primer--Os08g0484500 R:
                                  (SEQ ID NO. 7)
5'-CCGTCTAGAGAGCCCCAAAGATGGGATGT-3'.
```

Approximately 3,000 bp DNA fragment of wild-type (WT) and mutant (MU) genomic sequences of the OsESL1 gene were cloned. The total volume of a PCR system was 50 μl: rice genomic DNA template 1 μl (approximately 200 ng); 10× PCR buffer for KOD 5 μl; 25 mM MgSO$_4$ 3 μl; 2 mM dNTPs 5 μl; 105 μM primers, each for 1.5 μl; 1 U KOD (TOYOBO); diluting to 50 μl with ddH$_2$O. The reaction program was as follows: 35 cycles of denaturation at 94° C. for 5 min, 94° C. for 40 s, 55° C. for 40 s, and 68° C. for 4 min 30 s; and extension at 68° C. for 5 min.

The pCAMBIA 2300 vector and the above PCR amplified products were digested with restriction endonucleases SmaI and XbaI; a molar ratio of digested vector fragment to PCR product fragment was allowed to be 1:3; at room temperature, 1 μl of T4 DNA ligase was added, and finally the volume was diluted to 10 μl with water. After flicking the outer wall and mixing well, rapid centrifugation was conducted briefly, followed by incubation overnight at 16° C. The resulting ligation product was transformed into *Escherichia coli* DH5α; recombinant vectors pCAMBIA 2300-WT and pCAMBIA 2300-MU were obtained by restriction enzyme digestion and sequencing; subsequently, pCAMBIA 2300-WT and pCAMBIA 2300-MU were verified by sequencing. If correctly verified by sequencing, both vectors may be used for downstream experiment.

(2) Obtaining of Transformation Lines and Phenotypic Identification Thereof

Figure 8:
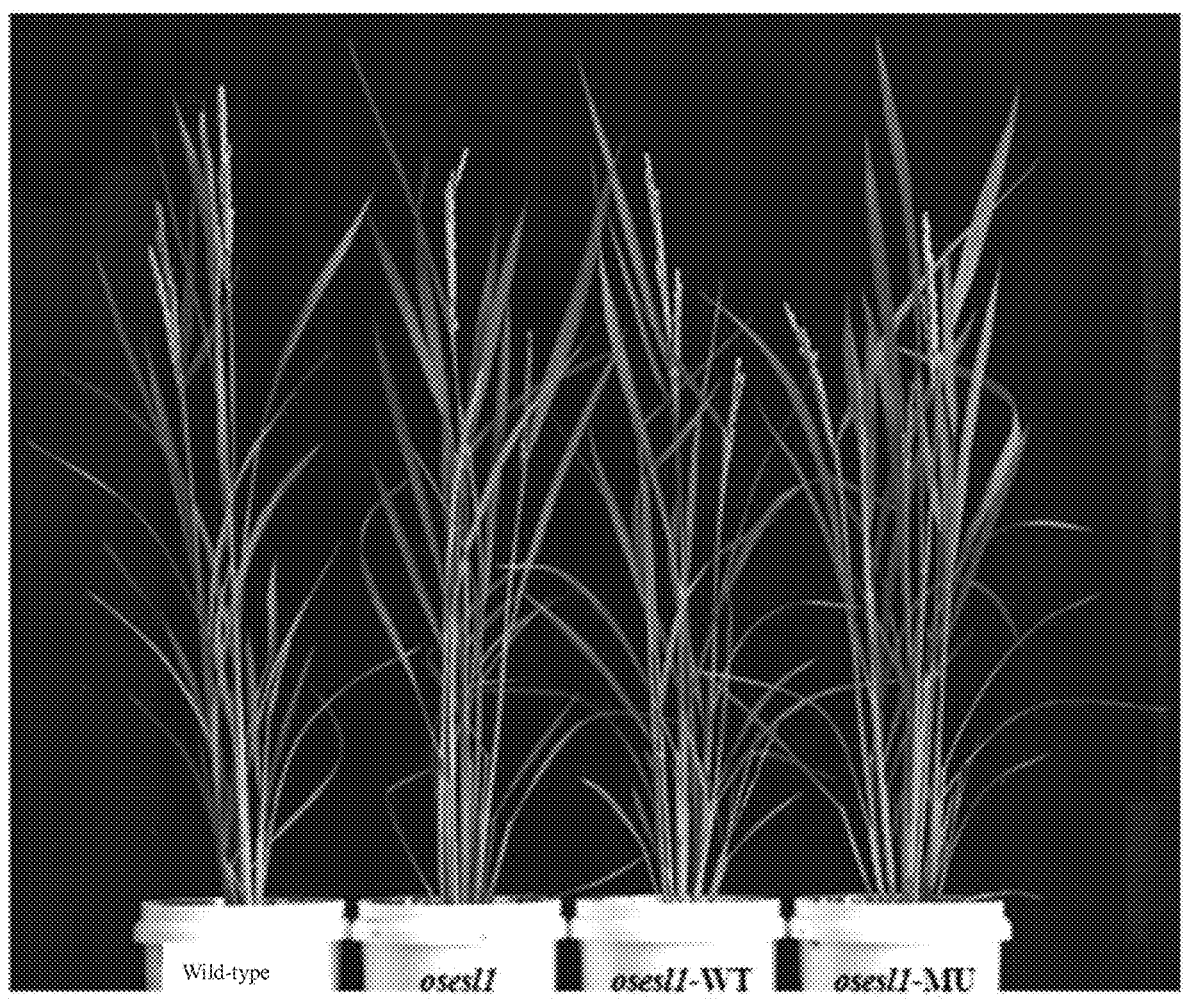
FIG. 8 illustrates phenotypes of growth and development of rice environmental conditional-lethal mutant osesl1 and T2 transgenic plants.
Figure 9:
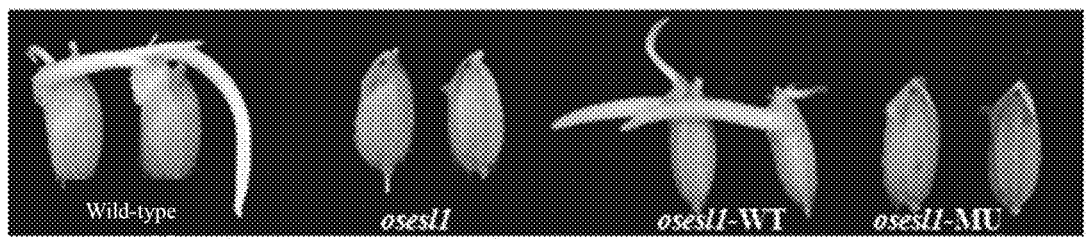
FIG. 9 illustrates lethal phenotypes of seeds of rice environmental conditional-lethal mutant osesl1 and T2 transgenic plants.

The well-constructed recombinant vectors pCAMBIA 2300-WT and pCAMBIA 2300-MU were transformed into EHA105 *Agrobacterium* strain, and further into osesl1 mutants using the *Agrobacterium*-mediated genetic transformation method (Hiei et al. Efficient transformation of rice (*Oryza sativa* L.) mediated by *Agrobacterium* and sequence analysis of the boundaries of the T-DNA. Plant Journal 1994, 6:271-282). Screened positive T0 transgenic plants were planted in the paddy field to obtain T1 seeds; T1 generations selfed to obtain T2 seeds. OsESL1 genes with both OsESL1 genotype and overexpressed wild-type and mutant-type were identified from T2 generations, and phenotypical reversion of these plants was observed. It was indicated that: mutant and transgenic plants were not significantly different from the wild-type during growth and development (FIG. 8); transformation of T2 transgenic plants with mutated OsESL1-MU vector still exhibited a seed embryonic lethal phenotype, but transformation of T2 transgenic plants with OsESL1-WT (wild-type gene) vector restored the wild-type phenotype (FIG. 9), suggesting that the embryo lethal phenotype was caused by the missense mutation in the above single base.

EXAMPLE 5

Study of Illumination and Temperature on osesl1 Mutant Gene

In two-line male sterile lines, the fertility of thermo-sensitive male sterile line had a critical transition temperature of 23.5° C.: sterile at >23.5° C.; otherwise, fertile. Differences in genetic background and research method led to different thermo-sensitive phases of different male sterile lines. The fertility of photoperiod sensitive male sterile line and fertility alteration thereof were influenced by photoperiod. In the sensitive period, the photoperiod was 13.45 h; when the photoperiod was <13.45 h, pollen fertility began to restore gradually. However, the photoperiod only induced the fertility thereof in a particular period, i.e., sensitive period; the temperature played a dominant role in the fertility of photo-thermo-sensitive male sterile line; under long-day and low-temperature conditions, the photo-thermo-sensitive male sterile line was partially fertile; under short-day and high-temperature conditions, the fertility decreased in varying degrees, suggesting that photoperiod-sensitive sterility was influenced by both illumination and temperature.

Osesl1 mutant also had a seed embryo conditional-lethal feature similar to the fact that the fertility of the male sterile line was controlled by illumination and temperature. The mutant exhibited as follows: in osesl1 homozygous mutants, seed embryos were lethal in Northern China in summer under long-day and high-temperature conditions, whereas seed embryos returned to wild-type phenotypes in Southern China in winter under short-day and low-temperature conditions.

Figure 10:
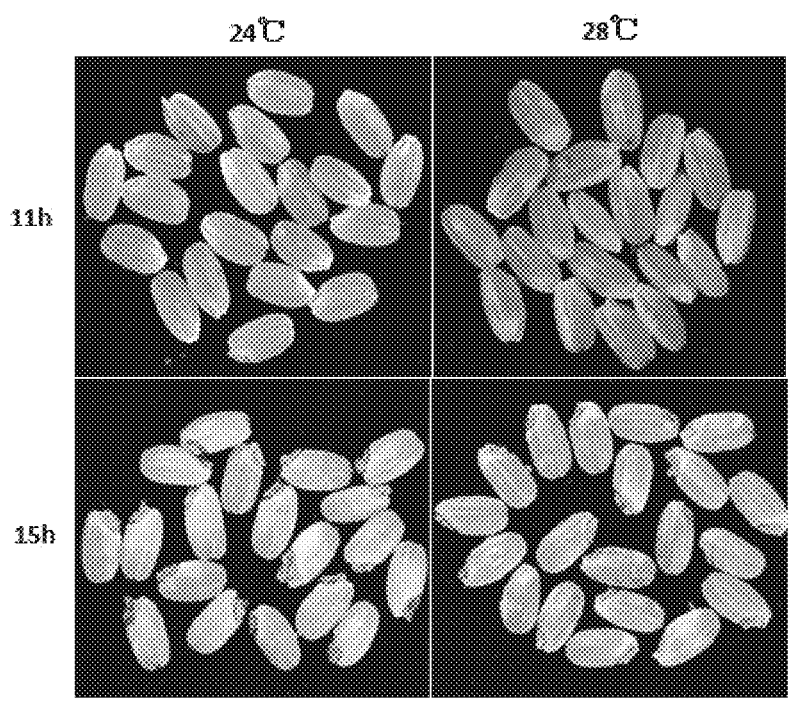
FIG. 10 illustrates long and short daylight conditions of rice environmental conditional-lethal mutant osesl1 and wild-type plants within a critical temperature range.

Osesl1 mutants were treated at different temperatures (22° C., 24° C., 26° C., 28° C., and 30° C.) for different photoperiods (10 h, 13 h, 14 h, and 15 h). It was found that: the critical temperature ranged between 24° C. and 28° C. for seed embryonic lethality of osesl1 mutants. Within this critical temperature range, when the photoperiod lasted for >13 h per day, seed embryos were dead; when the photoperiod lasted for <13 h per day, seed embryos developed normally (Table 4). At a temperature of <24° C., regardless of photoperiod, all seed embryos developed normally; at a temperature of >28° C., the seed embryonic lethality was not regulated by the photoperiod (FIG. 10).

TABLE 4

Analysis of lethality of osesl1 mutant gene under different illumination-temperature conditions

| Critical temperature (° C.) | Photoperiod (h) | Lethality (%) |
|---|---|---|
| 24 | 11 | 4.78% ± 3.33% |
| 24 | 13 | 99.58% ± 1.04% |
| 24 | 15 | 100% ± 0.00% |
| 26 | 11 | 25.20% ± 31.00% |
| 28 | 11 | 6.45% ± 14.88% |
| 28 | 13 | 96.74% ± 4.30% |
| 28 | 15 | 100% ± 0.00% |

| Extreme temperature (° C.) | Photoperiod (h) | Lethality (%) |
|---|---|---|
| >30 | 10 | 99.5% ± 1.25% |
| >30 | 14 | 99.5% ± 0.00% |
| 22 | 10 | 0.00% ± 0.00% |
| 22 | 14 | 0.00% ± 0.00% |

In view of the fact that illumination-temperature-related lethal conditions of the osesl1 mutant are wider than the critical temperature and photoperiod of the photo-thermo-sensitive male sterile line, such recessive trait further guarantees the breeding of two-line hybrid rice. If the OsESL1 gene is introduced into the two-line male sterile line, seed embryo lethal phenotype of the OsESL1 genotype appears at the late stage of pollen fertility; process of embryo development is accompanied by a gradual increase in environmental temperature. Even if the male sterile line becomes fertile due to temperature changes at the early stage, temperature rising at the late stage kills selfed seed embryos to guarantee safe seed production. Table 5 summarizes illumination-temperature conditions of safe seed production and multiplication. However, if the OsESL1 gene is introduced into restorer lines, seed multiplication will be conducted along with male sterile lines in long-day and high-temperature regions; because the seed embryonic lethality of the OsESL1 genotype omits the independent harvest of parent restorer lines, together with male sterile lines with the same growth period, mixed sowing and harvesting can be allowed, and fully mechanized farming can be realized to improve the seed production efficiency of hybrid rice. Either male sterile line or restorer line can be subjected to seed multiplication under short-day and low-temperature conditions.

TABLE 5

Illumination-temperature conditions of safe seed production and multiplication of male sterile and restorer lines of the OsESL1 genotype

| Male sterile or restorer line of osesl1 | Low temperature (<22° C.) | Low temperature (<24° C.) | High temperature (>24° C.) | High temperature (>30° C.) |
|---|---|---|---|---|
| Short day (<13 h) | Safe seed multiplication | Seed multiplication | Not suitable for seed production or multiplication | Safe seed production |
| Long day (>13 h) | Safe seed multiplication | Guaranteed seed production | Seed production | Safe seed production |

What is claimed is:

1. A rice environmental conditional-lethal mutant gene osesl1, having the nucleotide sequence of SEQ ID NO: 1.

2. A protein encoded by the rice environmental conditional-lethal mutant gene osesl1 according to claim 1, having the amino add sequence of SEQ ID NO: 2.

3. A method for controlling seed embryo development of rice, comprising introducing the rice environmental conditional-lethal mutant gene osesl1 according to claim 1 into a rice seed embryo using backcrossing or genetic transformation.

4. The method of claim 3, further comprising controlling an environmental temperature to remain below 22° C. during growth of the rice seed embryo to make the rice seed embryo develop normally.

5. The method of claim 3, further including controlling an environmental temperature to remain between 22° C. and 28° C. during growth of the rice seed embryo, wherein the rice seed embryo is provided a light duration of less than thirteen hours to make the rice seed embryo develop normally.

6. The method of claim 3, further including controlling an environmental temperature to remain between 22° C. and 28° C. during growth of the rice seed embryo, wherein the rice seed embryo is provided a light duration of greater than thirteen hours to kill the rice seed embryo.

7. The method of claim 3, further including controlling an environmental temperature to remain above 28° C. to kill the rice seed embryo.

* * * * *